US012773116B2

(12) United States Patent
Sadri et al.

(10) Patent No.: US 12,773,116 B2
(45) Date of Patent: Oct. 27, 2026

(54) IMPLANTABLE PRESSURE SENSOR DRIFT DETECTION

(71) Applicant: TC1 LLC, St. Paul, MN (US)

(72) Inventors: Vahid Sadri, Atlanta, GA (US); Nima Badie, Gold River, CA (US); Michael Fonseca, Powder Springs, GA (US); Jason White, Marietta, GA (US); John Erik Moore, Roswell, GA (US)

(73) Assignee: TC1 LLC

( * ) Notice: Subject to any disclaimer, the term of this patent is extended or adjusted under 35 U.S.C. 154(b) by 248 days.

(21) Appl. No.: 18/399,365

(22) Filed: Dec. 28, 2023

(65) Prior Publication Data

US 2024/0268687 A1 Aug. 15, 2024

Related U.S. Application Data

(60) Provisional application No. 63/484,928, filed on Feb. 14, 2023.

(51) Int. Cl.
*A61B 5/0215* (2006.01)
*A61B 5/00* (2006.01)

(52) U.S. Cl.
CPC ........ *A61B 5/02156* (2013.01); *A61B 5/6846* (2013.01); *A61B 5/746* (2013.01); *A61B 2560/0223* (2013.01); *A61B 2562/0247* (2013.01)

(58) Field of Classification Search
CPC . A61B 5/02156; A61B 5/0215; A61B 5/6846; A61B 5/6876; A61B 2560/0223; A61B 2562/0247
See application file for complete search history.

(56) References Cited

U.S. PATENT DOCUMENTS 8,068,907 B2 * 11/2011 Mann ................. A61B 5/02156 607/9
11,330,981 B2 * 5/2022 Andersen ............... A61B 5/076
2003/0139677 A1 7/2003 Fonseca
2004/0106874 A1 6/2004 Eigler
(Continued)

OTHER PUBLICATIONS

International Search Report and Written Opinion for Application No. PCT/US23/86310 mailed Apr. 12, 2024 (16 pages).
(Continued)

*Primary Examiner* — Devin B Henson
(74) *Attorney, Agent, or Firm* — Dean D. Small; Carroll, Hoette & Butscher, LLC

(57) ABSTRACT

A controller is provided for calibrating an implantable pressure sensor. The controller includes one or more processors, and a memory coupled to the one or more processors, wherein the memory stores program instructions. The program instructions are executable by the one or more processors to receive, from an implantable pressure sensor, characteristics of interest related to a patient, determine an implantable pressure sensor parameter in real time based on the characteristics of interest related to the patient and provide a drift threshold related to the implantable pressure sensor parameter. The one or more processors are also configured to determine whether the drift threshold has been exceeded based on the implantable pressure sensor parameter and communicate an alert in response to determining the drift threshold has been exceeded.

23 Claims, 10 Drawing Sheets

(56) References Cited

U.S. PATENT DOCUMENTS

| | | | | |
|---|---|---|---|---|
| 2007/0088220 | A1 | 4/2007 | Stahmann et al. | |
| 2014/0155769 | A1* | 6/2014 | White | A61B 5/7282 600/485 |
| 2023/0165475 | A1* | 6/2023 | Minor | A61B 5/029 600/486 |
| 2025/0176838 | A1* | 6/2025 | Singh | A61B 5/6804 |

OTHER PUBLICATIONS

Bayram et al. "From concept drift to model degradation: An overview on performance-aware drift detectors", Elsevier, Amsterdam, NL, vol. 245, Mar. 29, 2022 (19 pages).
Office Action for corresponding EP Application No. 23848359.8 dated May 21, 2026 (6 pages).

* cited by examiner

IMPLANTABLE PRESSURE SENSOR DRIFT DETECTION

CROSS-REFERENCE TO RELATED APPLICATIONS

This application claims the benefit of U.S. Provisional Application No. 63/484,928 filed Feb. 14, 2023, titled "IMPLANTABLE PRESSURE SENSOR DRIFT DETECTION", the subject matter of which is hereby incorporated by reference in its entirety.

FIELD OF THE INVENTION

Embodiments herein relate generally to systems and methods for detecting and correcting drift in an implantable pressure sensor.

BACKGROUND OF THE INVENTION

Implantable pressure sensors are implanted within a patient and communicate wirelessly with external devices to provide patient data and information such as pressure readings. The implantable pressure sensor can wirelessly transmit periodic (e.g., daily) pulmonary artery pressure (PAP) measurements to clinicians using a pressure sensor implanted in the distal pulmonary artery of heart failure (HF) patients. Each implantable pressure sensor is calibrated at implant, typically to the mean PAP measured by invasive right heart catheterization (RHC). Once calibrated, subsequent PAP readings should be accurate, ideally matching any post-implant follow-up RHC measurements. However, over time, sometimes the PAP measurements have been observed to deviate from the true pressure values.

On occasion, microscopic leakage in the sensor cavity or suboptimal implant site selection (e.g., vessels that are too narrow or have acute angulation) result in variance, or drift, between a pressure reading of implantable pressure sensor and the actual pressure being measured. Once identified, the implantable pressure sensor can be recalibrated. Still, currently, identifying these implantable pressure sensors only occurs when a patient visits a clinician, and a reading is manually taken and compared to the measurement of the implantable pressure sensor. Until this occurs, the implantable pressure sensor provides inaccurate readings and measurements that can result in incorrect diagnoses and/or unwarranted medication changes. Consequently, a system and method that can identify measurement drifts in the implantable pressure season before a manual reading of a clinician is desired.

SUMMARY

In accordance with embodiments herein, a controller is provided for calibrating an implantable pressure sensor. The controller includes one or more processors, and a memory coupled to the one or more processors, wherein the memory stores program instructions. The program instructions are executable by the one or more processors to receive, from an implantable pressure sensor, characteristics of interest related to a patient, determine an implantable pressure sensor parameter in real time based on the characteristics of interest related to the patient and provide a drift threshold related to the implantable pressure sensor parameter. The one or more processors are also configured to determine whether the drift threshold has been exceeded based on the implantable pressure sensor parameter and communicate an alert in response to determining the drift threshold has been exceeded.

Optionally, the characteristics of interest include a systolic pulmonary artery pressure (sPAP) and a diastolic pulmonary artery pressure (dPAP). In one aspect, the implantable pressure sensor parameter is a distance between a dPAP and a sPAP (pPAP). In another aspect, to determine the implantable pressure sensor parameter includes using a first numerical method in real time using the characteristics of interest obtained by the implantable pressure sensor. In one example, the first numerical method is Wasserstein Distance. In another example, to determine whether the drift threshold has been exceeded comprises utilizing a second numerical method using the parameter determined using the first numerical method. In yet another example, the second numerical method includes utilizing a Hoeffding's Bound method. Optionally, the one or more processors are further configured to dynamically update the drift threshold in real time based on the characteristics of interest obtained by the implantable pressure sensor. In one embodiment, the drift threshold is manually input into the controller.

In accordance with embodiments herein, a method is provided for calibrating an implantable pressure sensor that includes obtaining, with the implantable pressure sensor, characteristics of interest related to a patient and determining, with a controller, an implantable pressure sensor parameter in real time based on the characteristics of interest related to the patient. The method can also include obtaining a drift threshold related to the implantable pressure sensor parameter, determining, with the controller, whether the drift threshold has been exceeded based on the implantable pressure sensor parameter, and recalibrating, with the controller, the implantable pressure sensor.

Optionally, the method also includes communicating, with the controller, an alert in response to determining the drift threshold has been exceeded. In one aspect, the method can also include conducting an invasive right heart catheterization (RHC) in response to receiving the alert to verify the drift threshold has been exceeded, and recalibrating the implantable pressure sensor in response to verifying the drift threshold has been exceeded by the RHC. In another aspect, obtaining the drift threshold comprises dynamically updating the drift threshold in real time based on the characteristics of interest related to the patient. In one example, determining the implantable pressure sensor parameter comprises using a first numerical method in real time using the characteristics of interest obtained by the implantable pressure sensor. In another aspect, determining whether the drift threshold has been exceeded comprises utilizing a second numerical method using the parameter determined using the first numerical method.

In accordance with embodiments herein, a computer program product is provided that can be a non-transitory computer readable storage medium comprising computer executable code to obtain characteristics of interest related to a patient from an implantable pressure sensor. The executable code can also determine an implantable pressure sensor parameter in real time based on the characteristics of interest related to the patient and provide a drift threshold related to the implantable pressure sensor parameter. The executable code to additionally determine whether the drift threshold has been exceeded based on the implantable pressure sensor parameter, communicate an alert in response to determining the drift threshold has been exceeded, and calibrate the implantable pressure sensor based on the alert.

Optionally, to determine the implantable pressure sensor parameter comprises using a first numerical method in real time using the characteristics of interest obtained by the implantable pressure sensor. In one aspect, to determine whether the drift threshold has been exceeded comprises utilizing a second numerical method using the parameter determined using the first numerical method. In another aspect, to provide the drift threshold, the drift threshold is dynamically calculated in real time. In one example, to provide the drift threshold, the drift threshold is received from a manual input.

DETAILED DESCRIPTION

I. Terms and Abbreviations

Figure 1:
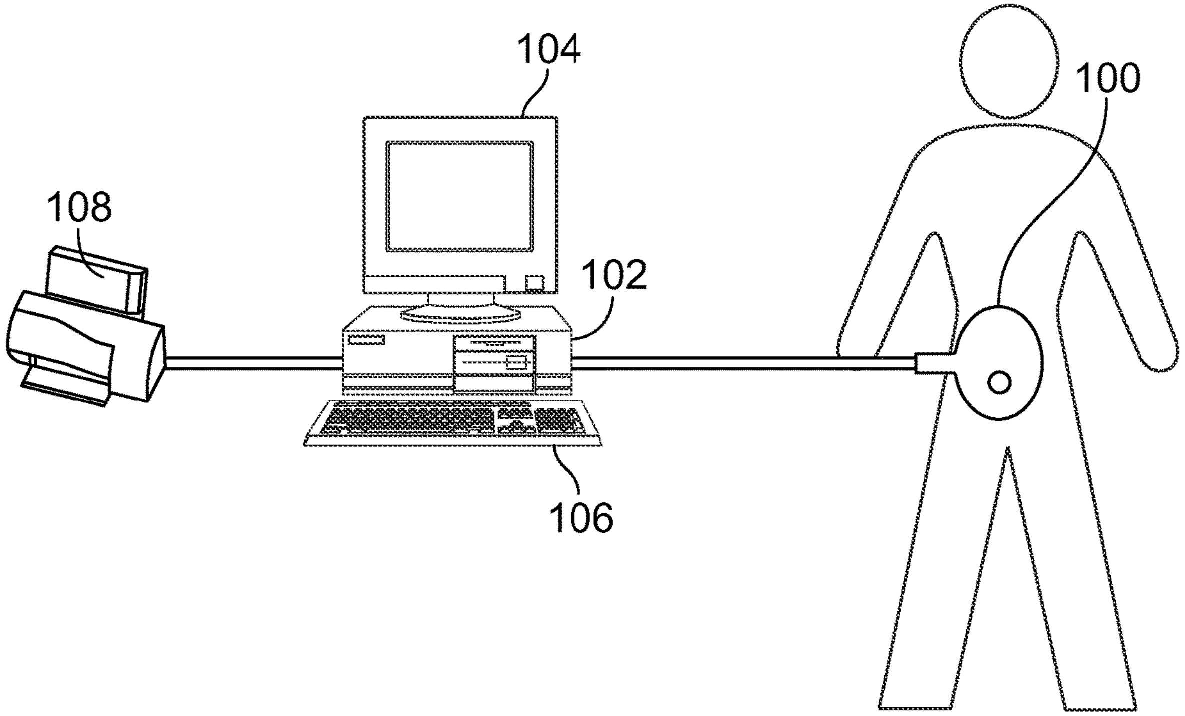
FIG. 1 illustrates a system for communicating with an implantable sensor in accordance with embodiments herein.

The term "drift" as used herein shall mean the amount by which a measurement, reading, data point, or the like is incorrect. Drift when described in relation to an implantable pressure sensor can be presented in any unit of measurement, including mmHG, that is measured or detected by the implantable pressure sensor. Drift can be determined via a mathematical equation, an algorithm, an artificial intelligence algorithm, model, mathematical model, using a Wasserstein Distance, using a Hoeffding's Bound method, or the like. A drift threshold is an amount or measurement where once exceeded, error in the measurement is considered enough to warrant recalibration.

The term "alert" shall mean any communication that conveys information or data related to a calibration of an implantable pressure sensor. The communication can be an output of the implantable pressure sensor, an output of an output device, server, remote device, or the like in communication with the implantable pressure sensor, an electronic mail, a text message, an auditory and/or vibratory message, etc. The communication can convey information to encourage a clinician to calibrate the implantable pressure sensor.

The phrase "characteristics of interest" as used here refers to any measurement, reading, data point, etc. obtained by an implantable pressure sensor. The characteristic of interest can be related to the patient and/or the implantable pressure sensor. Example characteristics of interest can include systolic PAP, diastolic PAP, other pressure measurements, or the like.

The phrase "implantable pressure sensor parameter" is any parameter, calculation, characteristic, etc. related to an implantable pressure sensor. In one example, a difference between the systolic PAP and diastolic PAP (e.g., pPAP) is an implantable pressure sensor parameter. The implantable pressure sensor parameter may be calculated, determined, obtained, or the like. When calculated, a first numerical method, second numerical method, model, algorithm, artificial intelligence algorithm, a combination of any of the previous, or the like may be utilized to make the calculation or determination.

The term "PAP" shall mean pulmonary arterial pressure.

The terms "processor," "a processor," "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The term "obtains" and "obtaining", as used in connection with data, signals, information, and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The term "calibrate," "calibrates," "calibration" and "calibrating" as used herein refers to any and all actions resulting in a sensor, such as an implantable pressure sensor, updating to a determined standard. Such calibration can be performed by the sensor itself by the changing of an implantable pressure sensor parameter. Alternatively, the sensor may be calibrated by a controller where the controller sends, transmits, provides, etc. a signal, command, instruction, or the like that is utilized to change or update the implantable pressure sensor parameter of the sensor. In this manner, one or more processors of a controller can calibrate a sensor such as an implantable pressure sensor.

The term "real-time" refers to a time frame contemporaneous with a normal or abnormal episode occurrence. For example, a real-time process or operation would occur during or immediately after (e.g., within minutes or seconds after) a cardiac event, a series of cardiac events, an arrhythmia episode, and the like.

II. System Overview

Provided are systems and methods that determine an estimated error, or drift, for readings or measurements (e.g., PAPs) obtained by an implantable pressure sensor. The drift can then be utilized to determine or identify when a PAP measurement has exceeded a drift threshold. Once the drift threshold is reached, a notification or alert can be communicated to a clinician recommending recalibration of the implantable pressure sensor.

In particular, correlation has been empirically observed between the pulse pressure amplitude (sPAP-dPAP) and mean PAP. This correlation has been determined to be linked to the compliance (Delta V/Delta P) of the pulmonary arterial system. As the mean pressure increases, the PA vasculature becomes taut (low compliance) and there is a greater delta P for the same delta V (stroke volume), due to the increased pressure required to create the same pulmonary arterial stretch (delta V) required to accommodate the new stroke volume. To this end, within the same patient, the relationship was consistent over time in cases where sensor mean pressure accuracy was confirmed via follow up RHC measurements. In cases where drift was detected in follow up RHC measurements, a deviation from the initial correlation between the pulse pressure and mean PAP (mPAP) was also observed. When the initial relationship was used to establish the relationship between pulse pressure and mean pressure, the estimated mean pressure can be determined based on the pulse pressure at any later point in time from the initial relationship. Meanwhile, the difference between the measured mPAP and the estimated mPAP can be an indication of drift in the sensor measured mPAP.

In making the determination that a PAP measurement has drifted more than a drift threshold from a true value, multiple example methodologies can be provided. In one example, the drift threshold may be dynamically updated with each reading utilizing numerical methods associated with characteristics of interest of the patient and implantable pressure sensor to provide the estimated drift threshold. In particular, by updating based on each reading, the drift threshold is dynamically updated. Alternatively, a less complex methodology can be provided where the drift threshold can be a static compared to measurements obtained by the implantable pressure sensor.

FIG. 1 illustrates an exemplary system for communicating with a wireless sensor implanted within a body. The system includes a coupling loop 100, a base unit 102, a display device 104 and an input device 106, such as a keyboard.

The display 104 and the input device 106 are used in connection with the user interface for the system. In the embodiment illustrated in FIG. 1 the display device and the input device are connected to the base unit. In this embodiment, the base unit also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface. In one embodiment, LABVIEW software is used to provide the user interface, as well as to provide graphics, store and organize data and perform calculations for calibration and normalization. The user interface records and displays patient data and guides the user through surgical and follow-up procedures.

An optional printer 108 is connected to the base unit and can be used to print out patient data or other types of information. As will be apparent to those skilled in the art other configurations of the system, as well as additional or fewer components can be utilized with the invention.

Patient and system information can be stored within a removable data storage unit, such as a portable USB storage device, floppy disk, smart card, or any other similar device. The patient information can be transferred to the physician's personal computer for analysis, review, or storage. An optional network connection can be provided to automate storage or data transfer. Once the data is retrieved from the system, a custom or third-party source can be employed to assist the physician with data analysis or storage.

The wireless sensor implanted in the body in example embodiments can include any sensor described in one or more of the following patents, all of which are expressly incorporated herein by reference in their entireties: U.S. Pat. No. 9,041,416 Titled "Physical Property Sensor with Active Electronic Circuit and Wireless Power and Data Transmission"; U.S. Pat. No. 9,653,926 Titled "Physical Property Sensor with Active Electronic Circuit and Wireless"; U.S. Pat. No. 8,264,240 Titled "Physical Property Sensor with Active Electronic Circuit and Wireless Power and Data Transmission"; U.S. Pat. No. 9,078,563 Titled "Method of Manufacturing Implantable Wireless Sensor for In-Vivo Pressure Measurement"; U.S. Pat. No. 7,621,036 Titled "Method of Manufacturing Implantable Wireless Sensor for In-Vivo Pressure Measurement"; U.S. Pat. No. 8,669,770 Titled "Selectively Actuating Wireless, Passive Implantable Sensor"; U.S. Pat. No. 7,909,770 Titled "Method for Using a Wireless Pressure Sensor to Monitor Pressure Inside the Human Heart"; U.S. Pat. No. 8,353,841 Titled "Apparatus and Method for Sensor Deployment and Fixation"; U.S. Pat. No. 8,118,749 Titled "Apparatus and Method for Sensor Deployment and Fixation"; U.S. Pat. No. 8,355,777 Titled "Apparatus and Method for Sensor Deployment and Fixation"; U.S. Pat. No. 8,021,307 Titled "Apparatus and Method for Sensor Deployment and Fixation; U.S. Pat. No. 9,265,428 Titled "Implantable Wireless Sensor"; U.S. Pat. No. 7,839,153 Titled "Communicating With An Implanted Wireless Sensor"; U.S. Pat. No. 7,699,059 Titled "Implantable Wireless Sensor"; U.S. Pat. No. 7,481,771 Titled "Implantable Wireless Sensor for Pressure Measurement within the Heart"; U.S. Pat. No. 6,855,115 Titled "Implantable Wireless Sensory for Pressure Measurement within the Heart"; U.S. Pat. No. 7,245,117 Titled "Communicating with Implanted Wireless Sensor"; U.S. Pat. No. 7,574,792 Titled "Method of Manufacturing an Implantable Wireless Sensor"; U.S. Pat. No. 7,498,799 Titled "Communicating with Implanted Wireless Sensor"; U.S. Pat. No. 7,492,144

Titled "Preventing False Locks in a System that Communicated with an Implanted Wireless Sensor"; U.S. Pat. No. 7,466,120 Titled "Communicating with an Implanted Wireless Sensor"; U.S. Pat. No. 7,550,978 Titled "Communicating with an implanted wireless sensor"; U.S. Pat. No. 7,439,723 Titled "Communicating with an Implanted Wireless Sensor"; U.S. Pat. No. 7,667,547 Titled "Loosely-Coupled Oscillator"; U.S. Pat. No. 8,111,150 Titled "Physiological Data Acquisition and Management System for use with an Implanted Wireless Sensor"; U.S. Pat. No. 7,710,103 Titled "Preventing False Locks in a System that Communicates with an Implanted Wireless Sensor"; U.S. Pat. No. 7,679,355 Titled "Communicating with an Implanted Wireless Sensor"; U.S. Pat. No. 6,159,156 Titled "Pressure Sensor for Use in an Artery"; U.S. Pat. No. 6,743,180 Titled "Pressure Sensor for Use in an Artery"; U.S. Pat. No. 8,237,451 Titled "Communicating with an Implanted Wireless Sensor"; U.S. Pat. No. 7,111,520 Titled "System and Method for the Wireless Sensing of Physical Properties"; U.S. Pat. No. 6,278,379 Titled "System, Method, and Sensors for Sensing Physical Properties"; and U.S. Pat. No. 8,665,086 Titled "Physiological Data Acquisition and Management System for Use with an Implanted Wireless Sensor".

FIGS. 2-7 present a first method for identifying or determining a drift in measurements that has occurred in an implantable pressure sensor and alerting a clinician accordingly. In this example, a method is provided to identify when a PAP measurement of the implantable pressure sensor has significantly (e.g., exceeded a drift threshold) from the true value. In particular, the pulse pressure (pPAP=systolic PAP [sPAP]-diastolic PAP [dPAP]) is accurate regardless of drift, and thus can be utilized as a reference. In one example, the sPAP and dPAP are considered characteristics of interest of a patient. While in this example sPAP and dPAP are the characteristics of interests obtained, in other examples other characteristics of interest of the patient can be obtained.

The distance between the pPAP and sPAP can be quantified using a numerical method that in one example embodiment can be a Wasserstein Distance (WD). The distance between the pPAP and sPAP (e.g., pPAP) is considered an implantable pressure sensor parameter. In one example, the implantable pressure sensor parameter can be obtained using characteristics of interest obtained by the implantable pressure sensor and thus is considered an implantable pressure sensor parameter. Generally, a WD is a distance function defined between probability distribution and a metric space. Once the WD is determined, another numerical method can be utilized in association with the WD to identify the drift. In one example, a Hoeffding's Bound drift detection algorithm with an exponentially weighted moving average ($HDDM_{W\text{-}test}$) is utilized to identify the drift. When a statistically significant variation for WD is detected by the $HDDM_{W\text{-}test}$ a drift exceeding a drift threshold is determined or identified.

Figure 2:
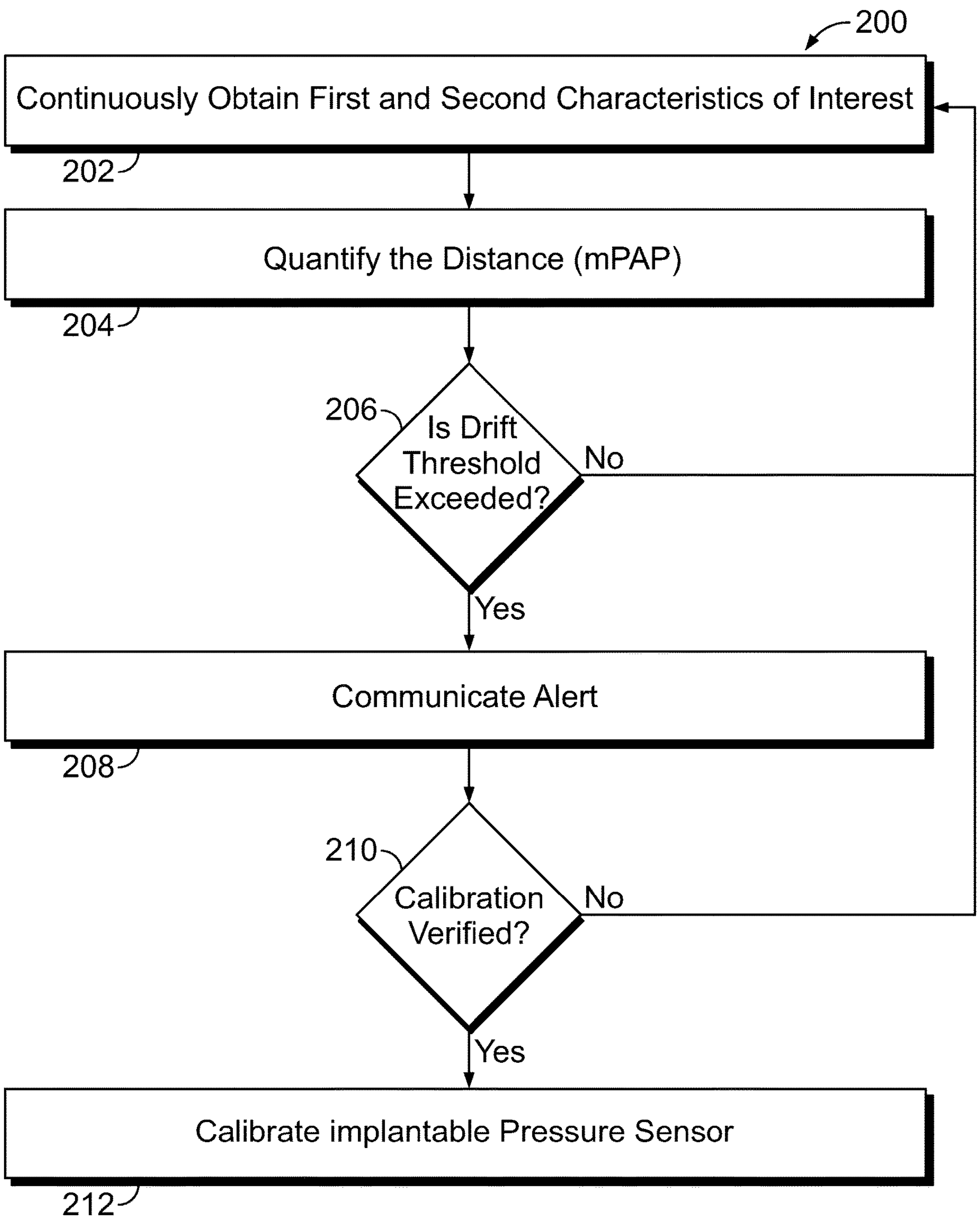
FIG. 2 illustrates a schematic flow block diagram of a method of calibrating an implantable pressure sensor in accordance with embodiments herein.

FIG. 2 presents a method 200 for calibrating an implantable pressure sensor. In one example, the implantable pressure sensor is the implantable pressure sensor presented in FIG. 1. At 202, one or more processors continuously obtain first and second patient characteristics of interest from the implantable pressure sensor. In one example, the first patient characteristic is a sPAP and the second patient characteristic is a dPAP.

At 204, one or more processors quantify the distance between the sPAP and dPAP utilizing a first numerical method in real time. In this manner, a implantable pressure sensor parameter is determined. In one example, the numerical method can be a WD, while in other examples other numerical methods may be utilized. In yet another example, an artificial intelligence algorithm is utilized that includes numerous variables and weight that are continuously adjusted to determine the implantable pressure sensor parameter. By utilizing a numerical method, algorithm, etc. to calculate a distance that is known as accurate, changes in measurements that result from patient activities and other changes are addressed. For example, disease progression, medication changes, exercising, eating, mood changes, sleeping, or the like can cause variations in the sPAP and dPAP that are not because of drift. Thus, by determining this distance, including adding significant accuracy through use of a numerical method such as determining a WD between the two, a drift threshold or variance of the drift is dynamic to account for the changes in the distance between the sPAP and dPAP. As a result, errors in determining that the drift is beyond a drift threshold are reduced, ensuring a clinician is only alerted when an actual drift has occurred.

Figure 3:
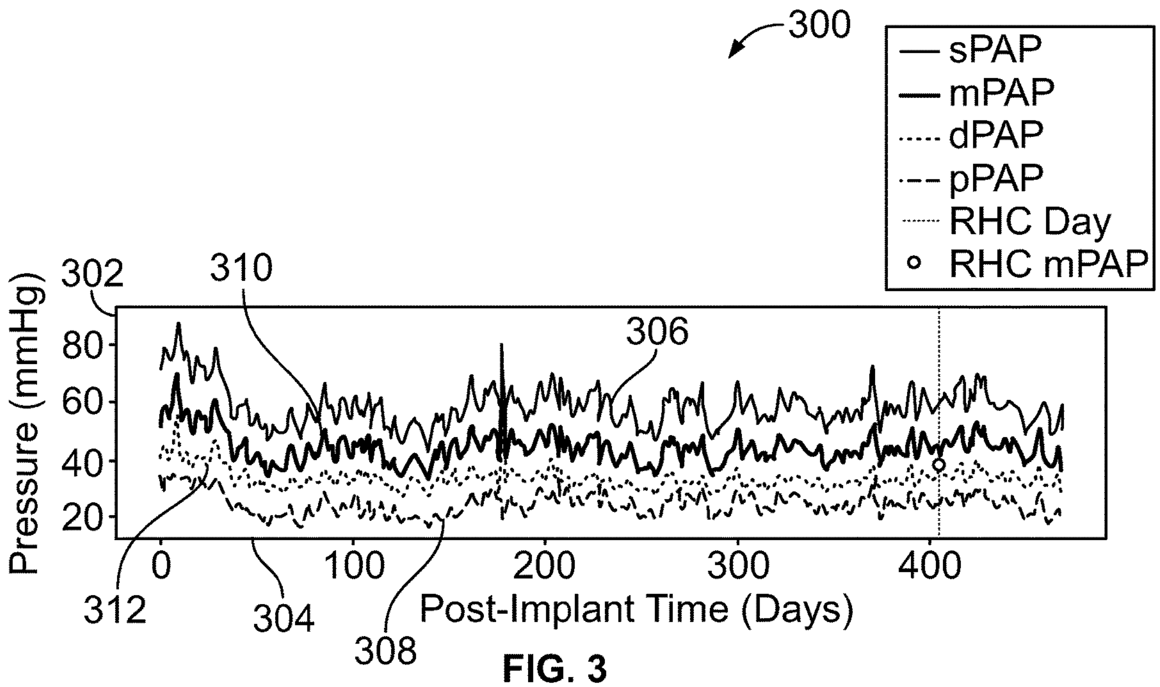
FIG. 3 illustrates a graph of pressure over time for an implantable pressure sensor in accordance with embodiments herein.
Figure 4:
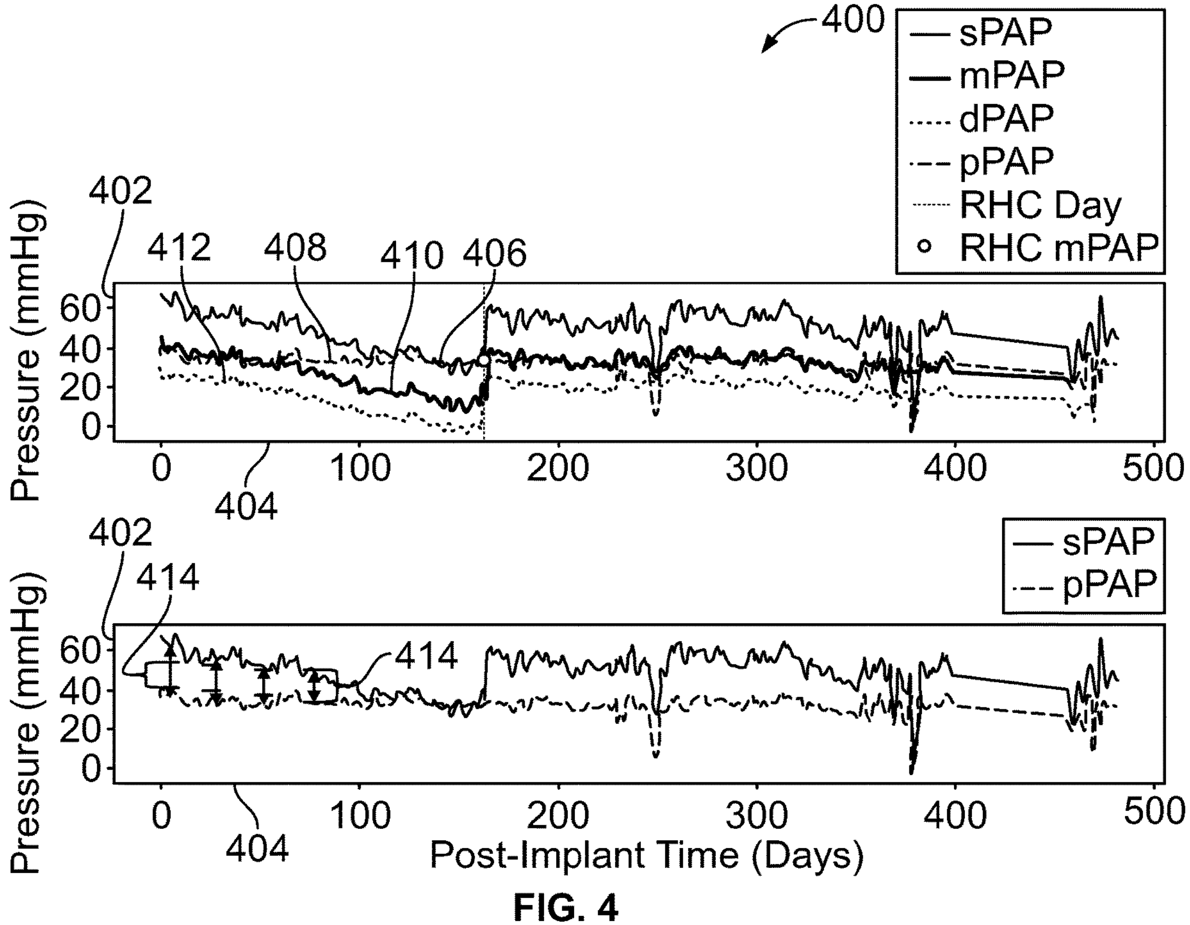
FIG. 4 illustrates a graph of pressure over time for an implantable pressure sensor in accordance with embodiments herein.
Figure 5:
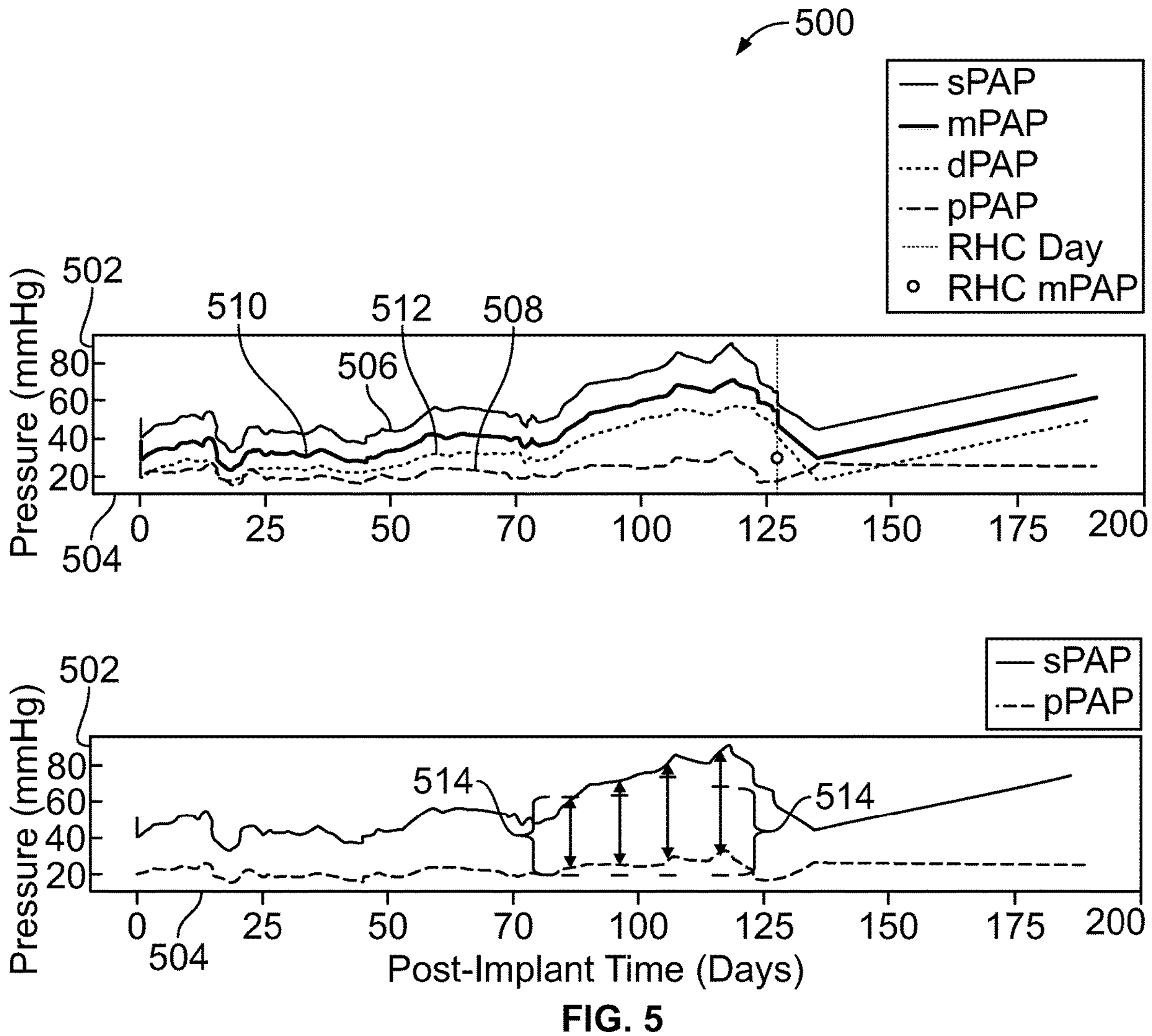
FIG. 5 illustrates a graph of pressure over time for an implantable pressure sensor in accordance with embodiments herein.

At 206, one or more processors determine whether a drift threshold has been exceeded based on the mPAP measurement. In one example, a numerical method can be utilized in making the determination. In one embodiment, a Hoeffding's Bound drift detection algorithm can be used to determine whether a drift threshold has been exceeded. FIGS. 3-5 present illustrations of how distances between sPAP and dPAP can be utilized in association with a drift detection algorithm to determine a drift threshold is exceeded to detect a drift. Each shows a graph 300, 400, 500 of an implantable pressure sensor that monitors pressure 302, 402, 502 (measured in mmHg) over time 304, 404, 504 (measured in days).

In the examples of FIGS. 3-5 long-term physiological changes in PAP are detected (e.g., as a result of disease progression, medication changes, or the like) where changes in mPAP are provided with concurrent and corresponding reduction in pPAP. In FIG. 3 the implantable pressure sensor displays no drift, and as a result a reduction in mPAP 310 is shown from day 0 to 50 post-implant, along with a corresponding reduction in pPAP 308. The RHC measurement 312 of mPAP is performed at day 405 showing the match to the implantable pressure sensor. As can be seen from FIG. 3, the distance between sPAP 306 and pPAP 308 is relatively constant over time.

In contrast, FIG. 4 illustrates an implantable pressure sensor that is providing inaccurately low measurements because of drift. A reduction in the mPAP 410 from day 0 to day 160 post-impact is provided, but without a corresponding reduction in pulse pressure pPAP 408. In addition, in the bottom panel of FIG. 4, illustrated is that the distance (e.g., difference) between sPAP 406 and pPAP 408 has decreased below a drift threshold 414. Thus, the implantable pressure sensor is demonstrating drift in mPAP over time that was confirmed by an RHC value 412 measured on day 160. As a result, the implantable pressure sensor should be calibrated.

Meanwhile, FIG. 5 illustrates an inaccurately high implantable pressure sensor where the measure of the distance between the sPAP 506 and pPAP 508 has increased above a drift threshold 514. In this example, the drift threshold is 10 mmHg. An increase in mPAP 510 from day 80 to day 120 post-implant is illustrated without a corresponding reduction in pPAP. As illustrated in the bottom panel of FIG. 5, the distance between sPAP 506 and pPAP 508 increased. The implantable pressure sensor demonstrates a drift in mPAP 510 over this time that was confirmed by an RHC value 512 measured on day 131 showing a drift of approximately 22 mmHG.

In one example, drift is identified by WD between sPAP and pPAP, using WD for inaccurately high sensors and WD inverse for accurately low sensors. The WD is then used to monitor each incoming reading by applying the drift detection method based on Hoeffding's inequality using the exponentially weighted moving average (EWMA) ($HDDM_{W\text{-}test}$), described below. When drift has occurred (e.g., for inaccurately low sensors), the distance between sPAP and pPAP is decreasing and therefore the WD inverse will increase, and whenever the $HDDM_{W\text{-}test}$ detects a statistically significant variation (e.g., a drift threshold is exceeded) in the WD inverse, the drift signal is triggered. A similar concept detects drift on inaccurately high sensors. This method is not based on any predefined pressure threshold and, due to the incremental learning nature of the $HDDM_{W\text{-}test}$ method, the algorithm will establish the baseline drift threshold for different conditions. In this manner the drift threshold can dynamically vary over time based on characteristics of interest of the patient.

Figure 6:
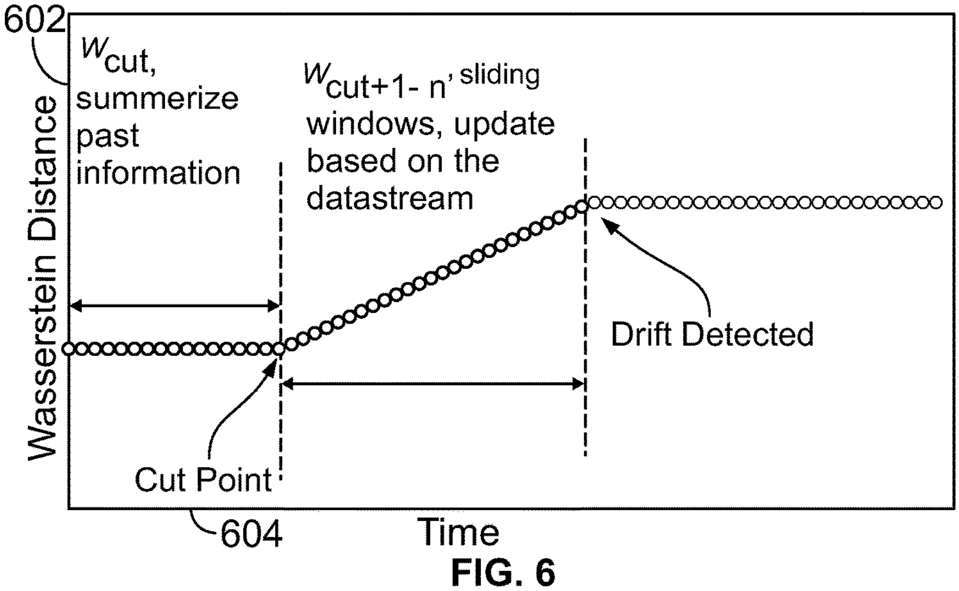
FIG. 6 illustrates a graph of Wasserstein Distance over time for an implantable pressure sensor in accordance with embodiments herein.

Consider a sequence of variables $X_1, X_2, \ldots, X_{cut}, X_{cut+1}, \ldots, X_n$ and the problem of detecting a significant increase in the mean value of this sequence, FIG. 6 that illustrates the WD 602 over time 604. For the exponentially weighted moving average (EWMA) statistic, where $X_n=(1-\lambda)\, X_{n-1}+\lambda X_n$ and $X_1, X_2 \ldots, X_n$ bounded in the interval [a, b]:

$$\mathbb{P}\left(\left|\mu_{W_{cut}} - \mu_{W_{cut+1-n}}\right| \geq \varepsilon_D\right) \leq e^{-\frac{2\varepsilon_D^2(2-\lambda)}{\lambda(b-a)^2}} \tag{1}$$

$$\varepsilon_D = (b-a)\sqrt{\frac{\lambda}{\lambda+2}\ln\frac{1}{\alpha_D}} \tag{2}$$

Wherein:

$\alpha_D \in (0,1]$: confident for the drift level (a user defined parameter)

$\lambda$: forgetting factor for EWMA (a user defined parameter)

$\varepsilon_D$: error bound $\mu_{W_{cut}}$: EWMA statistic computed from $X_1, X_2, \ldots, X_{cut}$ $\mu_{W_{cut+1-n}}$: EWMA statistic computed from $X_{cut+1}, \ldots, X_n$ Equation 1 is derived from Hoeffding's inequality and EWMA statistic. Now, to estimate the actual state (STABLE or DRIFT) of the samples $X_1, X_2, \ldots, X_{cut}, X_{cut+1}, \ldots, X_n$, if the Equation 1 does not hold, the null hypothesis is rejected with size ap, and the drift threshold is exceeded such that the change detector reaches the DRIFT level, and all counters are reset. Otherwise, the null hypothesis is accepted, the drift threshold is not exceeded, and the status is set to STABLE.

With reference back to FIG. 2, if a drift threshold is not exceeded and the implantable pressure sensor is STABLE, then the one or more processors continue to obtain first and second patient characteristics of interest from the implantable pressure sensor. However, if the drift threshold is exceeded, then at 208, the one or more processors communicate an alert to a clinician. In one example the clinician is at a remote location such as a clinician office, hospital or the like and receives the alert via a wireless communication protocol. The alert may be a message that identifies the implantable pressure sensor and the patient and indicates that calibration is required. The message can be a code, color, sound, chart, or the like that alerts the clinician that patient with the implantable pressure sensor should visit the clinician (or the clinician should visit the patient) to determine if calibration is needed. In one example, an appointment is automatically scheduled at the clinician's office. The one or more processors may access the calendar of both the patient and the clinician to provide a time. Alternatively, based on the amount of drift detected, a recommendation may be provided for a timeline (e.g., within a week, within a month, within two months) for the patient to visit the clinician.

At 210, the implantable pressure sensor is tested by a clinician to determine whether calibration of the implantable pressure sensor is required. In one example, an RHC value is measured. By having the implantable pressure sensor system disclosed that provides an alert upon a detection that a drift threshold has been exceeded, instead of just measuring the RHC value at a next visit to the clinician, the RHC value is measured concurrently (e.g., within a few day or a few weeks) with the detection of the drift threshold being exceeded. This can result in the reduction of hundreds of days from detection of the implantable pressure sensor that requires calibration. As a result, false readings and incorrect medication changes are avoided.

At 212, if confirmation is provided that the implantable pressure sensor has experienced drift, then the one or more processors calibrate the implantable pressure sensor. By calibrating the implantable pressure sensor, accurate readings can again be obtained, reducing incorrect diagnosis and treatments.

Figure 7:
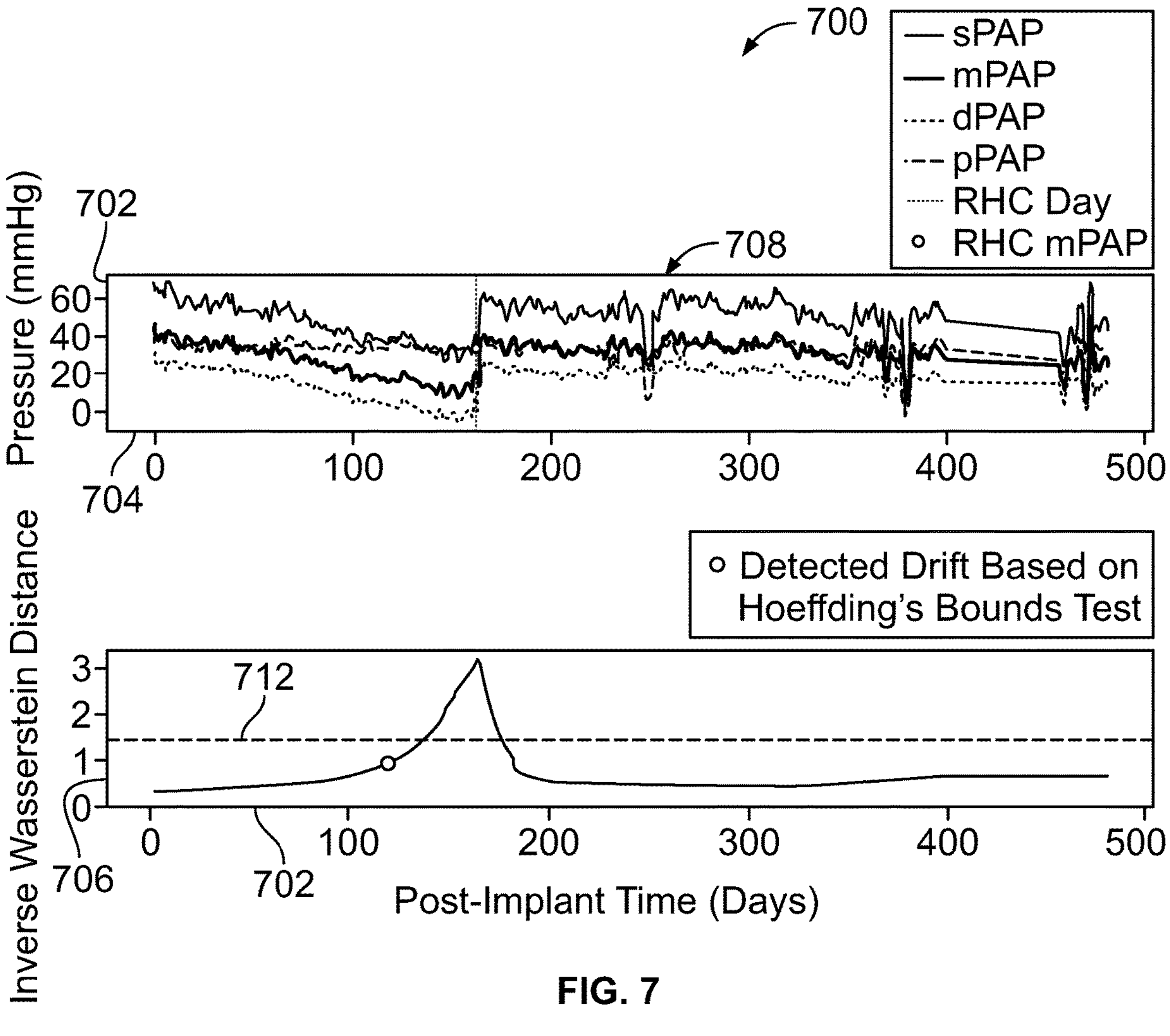
FIG. 7 illustrates pressure and Wasserstein Distance over time for an implantable pressure sensor in accordance with embodiments herein.

FIG. 7 illustrates how the method of FIG. 2 can be utilized to speed calibration of an implantable pressure sensor. In one example, the detailed functioning of the algorithm, including the configurable implantable pressure sensor parameters used, is described to identify whether the drift threshold is exceeded is as follows:

1. This algorithm needs two predefined values:
   a. $\alpha_D \in (0,1]$, confidence to the drift.
   b. $\lambda$: forgetting factor for EWMA. Smaller values mean less weight given to recent data.
2. Wasserstein distance (WD) between sPAP and pPAP is calculated from all readings collected beyond 14 days post-implant, across all readings for the previous 25 days. Wasserstein distance computes the distance between two vectors. Given two vectors $a \in$ sPAP [1, n], $b \in$ dPAP[1,m]:

$$WD(a, b) = inf\langle C, T\rangle \tag{3}$$

Where inf is infimum, C(i, j) represent the cost of moving a[i] to b[j] and in this algorithm it sets to one, T is an optimal transport solution between vectors a and b and U(a, b), where U(a, b) is set of all non-negative n×m matrices with row and column sums a, b respectively.
3. The algorithm monitors WD, for detecting possible inaccurate high sensor, and $$WD_{inverse} = \frac{1}{10WD}$$

for detecting possible inaccurate low sensors.
4. Bothe WD and $WD_{inverse}$ monitors by $HDDM_{W\text{-}test}$ algorithm with the following implantable pressure sensor parameters:

For $WD$: $\alpha_{D\_inacc\_high} = 0.035$, $\lambda_{inacc\_high} = 0.0005$ i.

For $WD_{inverse}$: $\alpha_{D\_inacc\_low} = 0.035$, $\lambda_{inacc\_low} = 0.08$ ii.

5. The drift threshold being exceeded is identified when the null hypothesis based on Eq. 1 is rejected with size $\alpha_D$ for either WD or $WD_{inverse}$.
6. If/when the sensor is recalibrated, the WD is recalculated for all readings beginning at 14 days post-calibration.

To this end, FIG. 7 illustrates a graph 700 of an implantable pressure sensor with the top panel measuring pressure 702 over time 704 and the bottom panel measuring the inverse WD 706 over time 702 utilizing the methodology as provided in FIG. 2. The top panel of FIG. 7 shows the PAP measurements 708 from the same drifted sensor from FIG. 4 and includes the inverse of WD 706 in the bottom panel. The 25-day moving average of WD is calculated daily for each reading of the implantable pressure sensor. While the implantable pressure sensor starts drifting, the distance between sPAP and pPAP decreases and, therefore, the inverse of WD 706 increases. Whenever the increase in WD inverse 706 reaches the statistical signifying level (e.g., drift threshold) 712, as defined by the user, the $HDDM_{W\text{-}test}$ detects the drift threshold has been exceeded. In this example, the drift threshold was exceeded and identified at day 120 post-implant, approximately 42 days earlier than a RHC procedure, when drift would be observed in clinic without using the methodology of FIG. 2. The bottom panel illustrates that after recalibration at day 162, the mPAP is elevated and the WD inverse 706 returns to a value that does not exceed the drift threshold.

In using the methodology of FIG. 2 a database was assembled that consisted of daily sPAP and pPAP readings and follow-up RHC measurements for numerous implantable pressure sensors, including implantable pressure sensors that did and did not demonstrate drift. In addition, implantable pressure sensors with recalibrations performed prior to the RHC follow-up were excluded. Implantable pressure sensors having a drift threshold that was exceeded were defined as those implantable pressure sensors with absolute differences between the and RHC mPAP values ≥10 mmHg. Implantable pressure sensors that exceeded a drift threshold identified by the algorithm were defined as those in which drift was detected at any time from implant to the RHC follow-up. Each sensor was then classified as follows:

TP (true positive): Drift was observed at the time of RHC follow-up, and drift was identified by the algorithm at any time from implant to RHC follow-up.

TN (true negative): Drift was not observed at the time of RHC follow-up, and drift was not identified by the algorithm at any time from implant to RHC follow-up.

FP (false positive): Drift was not observed at the time of RHC follow-up, but drift was identified by the algorithm at any time from implant to RHC follow-up.

FN (false negative): Drift was observed at the time of RHC follow-up, but drift was not identified by the algorithm at any time from implant to RHC follow-up.

Using these classifications, the following performance metrics were calculated:

Sensitivity=% of drifted sensors that were accurately detected=TP/(TP+FN)

Specificity=% of non-drifted sensors that were accurately detected=TN/(TN+FP)

Positive Predictive Value (PPV)=% of drift-detected sensors that truly drifted=TP/(TP+FP)

Negative Predictive Value (NPV)=% of non-drift detected sensors that truly did not drift=TN/(TN+FN)

Drift Detection Benefit=#days prior to RHC follow-up that the algorithm appropriately detected drift (for TP only)

For 287 implantable pressure sensors evaluated in the database the resulting performance metrics are as follows:

Sensitivity=62.1%

Specificity=71.4%

PPV=54.7%

NPV=77.2%.

Drift Detection Benefit=median 316 days [IQR; 151:531 days]

For the 55 sensors evaluated as part of the US PAS database (testing dataset), 13 TPs, 5 FPs, 32 TNs, and 5 FNs where the resulting performance metrics are as follows:

Sensitivity=72.2%

Specificity=86.5%

PPV=72.1%

NPV=86.4%

Drift Detection Benefit=median 123 days [IQR; 48:354 days]

For US PAS database, the algorithm identified 72.2% of sensors that ultimately exhibited drift at the time of RHC (sensitivity), 72.1% of all sensors identified as having drifted by the algorithm did truly drift (PPV). In those sensors, the drift was identified 123 days earlier than the RHC procedure, potentially avoiding inaccurate diagnoses or medication changes.

In all, when a determination is made that the drift threshold has been exceeded, a notification can automatically be sent to the assigned clinician, indicating that recalibration is recommended. While the implantable pressure sensor parameter of the method of FIG. 2 has been described as the WD, in an alternative approach the distance between sPAP and pPAP can be quantified by any other mathematical distance, e.g., energy distance, or the like. In another alternative approach the WD can be monitored by any other drift algorithm detection, (e.g., Early Drift Detection Method, ADWIN (ADaptive WINdowing), or Kolmogorov-Smirnov Windowing method. In yet another alternative approach the WD can be quantified between dPAP and pPAP [WD(dPAP, pPAP)] or mPAP and pPAP [WD(mPAP, pPAP)] and monitored by a drift algorithm detection. In still yet another alternative approach the WD can be quantified between WD(dPAP, pPAP) and WD(sPAP, pPAP) and monitored by any drift algorithm detection. Optionally, the drift detection "sensitivity" can be programmable (e.g., low, medium, high) by adjusting the drift threshold. This may be critical when an algorithm is used in conjunction with other algorithms, and a high drift detection sensitivity is required (lower difference threshold) to refrain from providing medication recommendations for all sensors in which drift is suspected. The drift detection "sensitivity" for inaccurate high and low implantable pressure sensors can be programmed by difference threshold. This may be critical when this algorithm is used in conjunction with other algorithms, a higher drift detection sensitivity is required for inaccurate high sensor while it could cause health risks for the patients by prescribing aggressive medications.

FIGS. 8-11 illustrate another method and accompanying graphs for identifying or determining a drift in measurements that has occurred in an implantable pressure sensor and alerting a clinician accordingly. In this example a method is provided to identify when the mean PAP measurement of an implantable pressure sensor has significantly drifted from its true value (e.g., has a drift threshold that is exceeded). Early identification of sensor drift may mitigate incorrect diagnoses or medication changes. This drift detection method is based on the observation that implantable pressure sensors with drifting mean PAP (mPAP) values demonstrate this change in mPAP without a corresponding change in pulse pressure, defined as the difference between the sPAP and dPAP. Physiologically, the ratio "R" between pulse pressure and mean pressure should remain stable for each patient over time. Thus, this ratio (R=[sPAP−dPAP]/mPAP) can be calculated at implant before any drift has occurred ($R_0$) and used at each subsequent implantable pressure sensor reading to back-calculate an estimated mPAP ($mPAP_{est}$). At each subsequent reading, $mPAP_{est}$=(sPAP−dPAP)/$R_0$. Drift can then be identified when the current mPAP value differs from $mPAP_{est}$ beyond a defined drift threshold (e.g., ±15 mmHg). In this manner, the characteristics of interest sPAP and dPAP can be utilized to determine an implantable pressure sensor parameter ($mPAP_{est}$) that can then be used to determine if a drift threshold has been exceeded.

Figure 8:
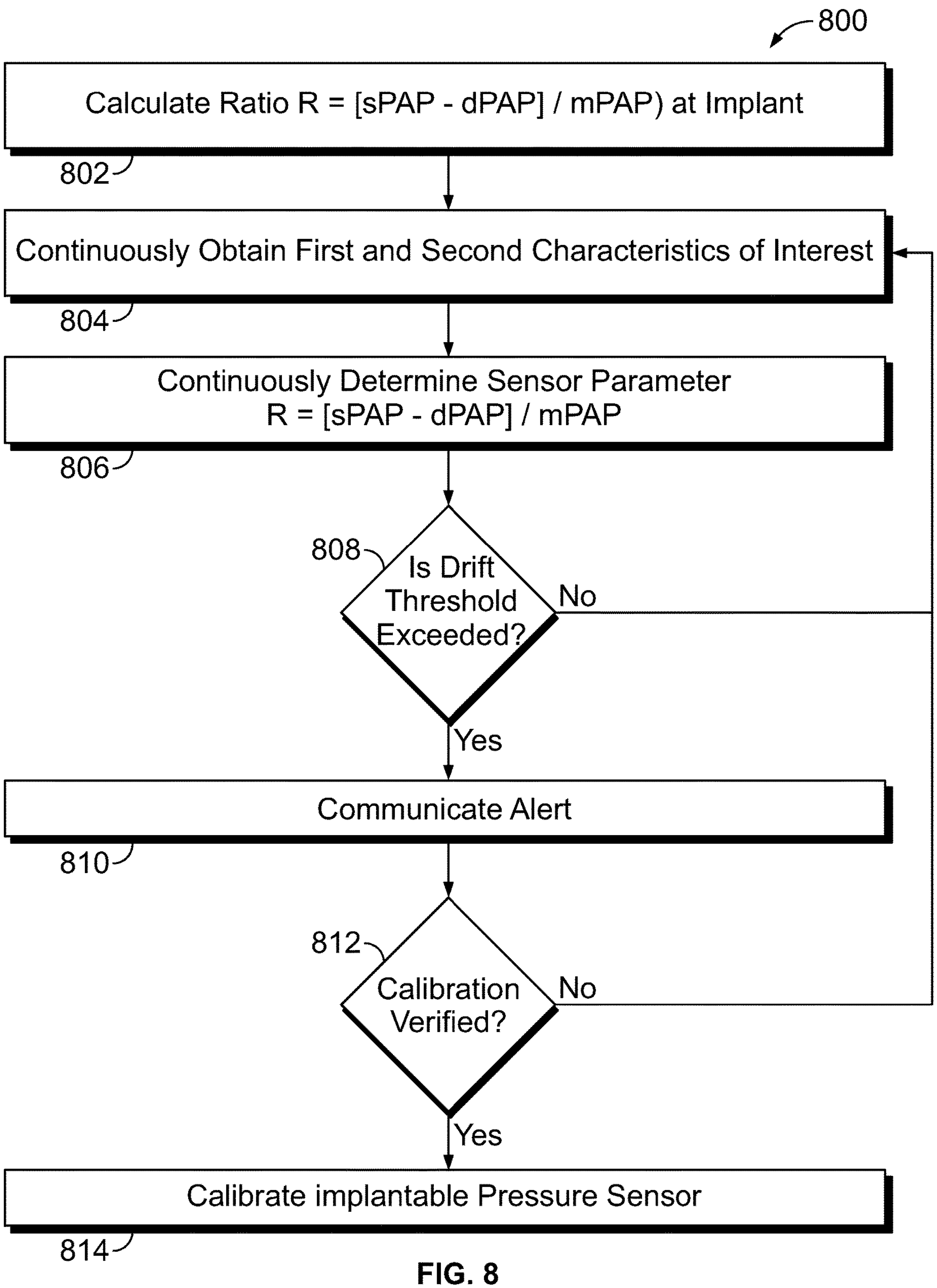
FIG. 8 illustrates a schematic flow block diagram of a method of calibrating an implantable pressure sensor in accordance with embodiments herein.

FIG. 8 provides a method 800 for calibrating an implantable pressure sensor. In one example, the implantable pressure sensor is the implantable pressure sensor presented in FIG. 1. At 802, one or more processors calculate a ratio (R=[sPAP−dPAP]/mPAP) when an implantable pressure sensor is implanted into a patient and before any drift has occurred. In one example, the initial ratio is designated as ($R_0$).

At 804, the one or more processors continuously obtain first and second patient characteristics of interest from the implantable pressure sensor. In one example, the first patient characteristic is a sPAP and the second patient characteristic is a dPAP. To this end, at 806, the one or more processors continuously determine an implantable pressure sensor parameter that is R=[sPAP−dPAP]/mPAP) in real time based on the obtained first and second patient characteristics. By obtaining the first and second patient characteristics of interest the ratio can be continuously determined and compared to the initial ratio $R_0$ to determine if a drift threshold has been exceeded.

Figure 9:
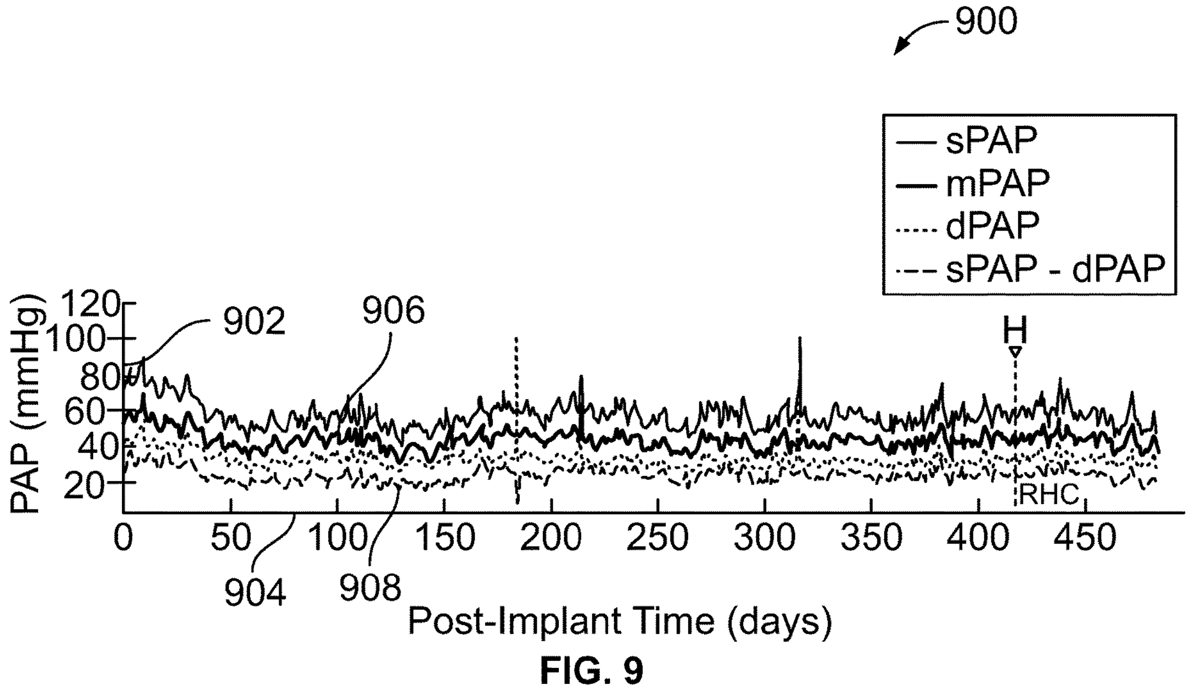
FIG. 9 illustrates a graph of PAP over time for an implantable pressure sensor in accordance with embodiments herein.

At 808, the one or more processors determine whether a drift threshold has been exceeded based on the ratio. As illustrated in FIG. 9, during long-term physiological changes in PAP (e.g., resulting from disease progression or medication changes), changes in mPAP are observed with concurrent and corresponding changes in pulse pressure (sPAP-dPAP).

FIG. 9 illustrates a graph 900 showing PAP 902 (in mmHG) over time 904 (in days) of an implantable pressure sensor that does not present drift. As shown in FIG. 9, a reduction in mPAP 906 is shown from day 0 to day 50 post-implant, along with a corresponding reduction in pulse pressure 908. The right heart catheter (RHC) measurement of mPAP performed much later, at day 405 approximately matched the mPAP value 906 at that time. This implantable pressure sensor tracked changes in PAP 902 over time 904 and exhibited no drift and matched the follow-up RHC measurement.

Figure 10:
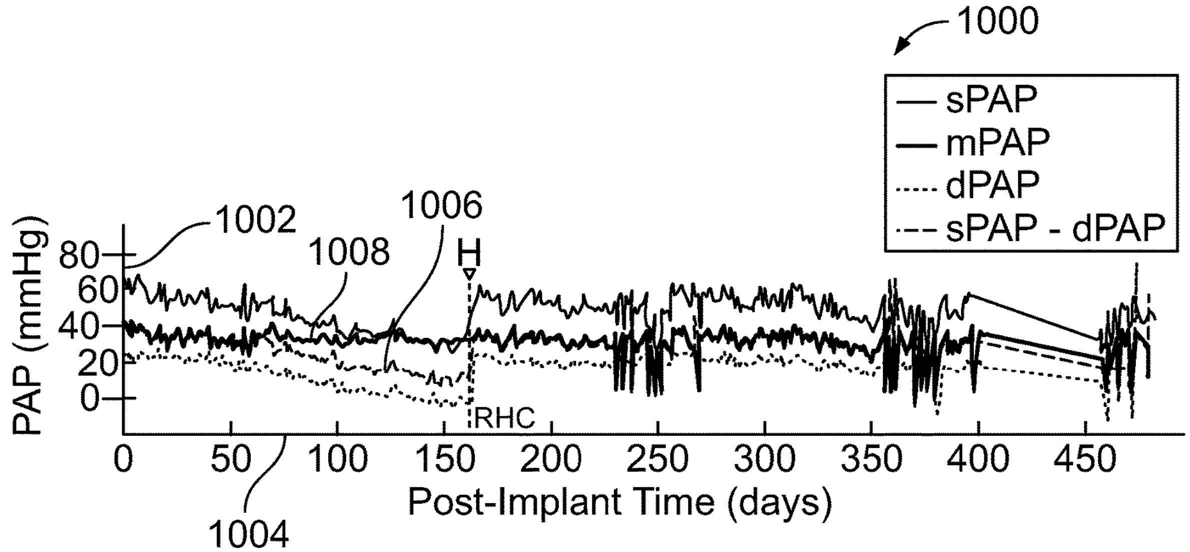
FIG. 10 illustrates a graph of PAP over time for an implantable pressure sensor in accordance with embodiments herein.

FIG. 10 again illustrates a graph 1000 showing PAP 1002 (in mmHG) over time 1004, only in this example the implantable pressure sensor does show drift that exceeds a drift threshold. The graph shows a reduction in mPAP 1006 from day 0 to day 160 post-implant, but without a corresponding reduction in pulse pressure 1008. This implantable pressure sensor demonstrated a drift in mPAP 1006 over this time, which was confirmed by the RHC value measured at day 160 (approximately 25 mmHg greater than the mPAP 1006 at that time). In this manner, if the drift threshold was set as 20 mmHG, the drift threshold is exceeded, indicating that recalibration of the implantable pressure sensor was required. FIG. 10 also shows that such recalibration occurred, and that drift no longer occurred thereafter.

As illustrated, by utilizing the ratio between pulse pressure and mean pressure, that should remain stable over time, implantable pressure sensors experiencing drift can be identified. First, the ratio (R=[sPAP−dPAP]/mPAP) is calculated from all nightly at-home readings taken between days 7 and 21 post-implant, and the median is used as the "baseline" ratio ($R_0$). The ratio is specific to each patient and should not change over time unless a recalibration is performed. The ratio is assumed to be accurate just after calibration at implant, before the mPAP has time to potentially drift. This $R_0$ baseline ratio can then be used to back-calculate an estimated mPAP ($mPAP_{est}$) for subsequent readings based on the new pulse pressure:

$$mPAP_{est} = (sPAP - dPAP)/R_0 \tag{4}$$

When drift has occurred, the mPAP measured by the implantable pressure sensor diverges from this calculated $mPAP_{est}$ value. Although mPAP may drift, (sPAP−dPAP) does not, because (sPAP−dPAP) is a difference between two PAP values. Thus, $mPAP_{est}$ is not susceptible to drift.

Figure 11:
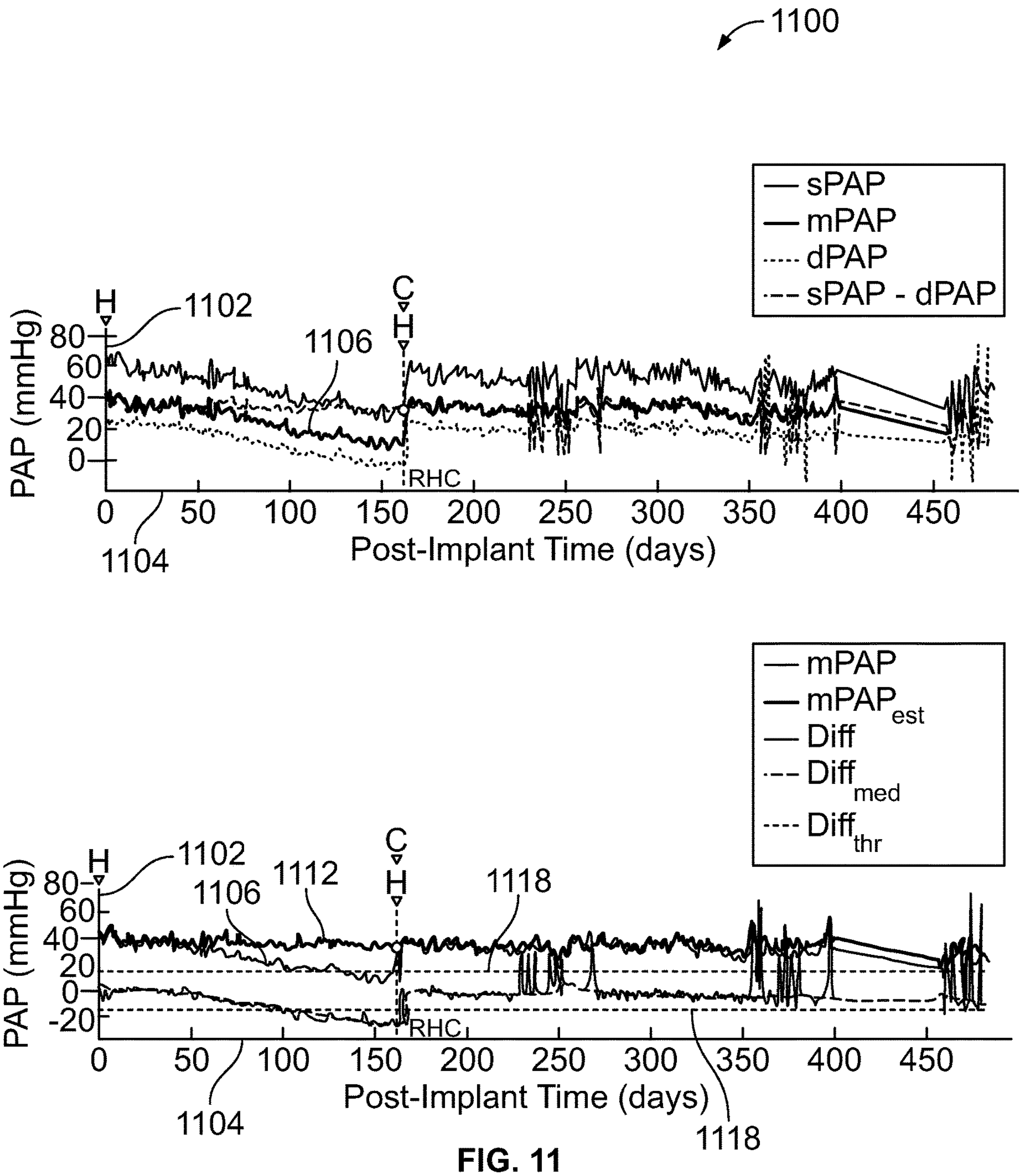
FIG. 11 illustrates a graph of PAP over time for an implantable pressure sensor in accordance with embodiments herein.

FIG. 11 illustrates graph 1100 of the implantable pressure sensor of FIG. 10 that is experiencing drift. The top panel shows the PAP measurements 1102 (in mmHG) over time 1104 (in days) like FIG. 10 and includes the difference between mPAP 1106 and $mPAP_{est}$ 1112 in the bottom panel. This difference can be calculated daily for each reading, and a moving median of the previous 3 weeks can be calculated. The algorithm detects drift when the 3-week median crosses a predefined drift threshold 1118 ("$Diff_{thr}$"=±15 mmHg). In this example, the threshold drift was exceeded at day 100 post-implant, approximately 60 days earlier than the RHC procedure, when drift was observed in clinic. After the RHC procedure was performed at day 160, the implantable pressure sensor was recalibrated, resulting in the mPAP being elevated to match $mPAP_{est}$ (and RHC mPAP) and the difference (Diff) returning to zero. In addition, drift may also result in the diastolic PAP exhibiting a non-physiologic negative value, independent of the ($mPAP-mPAP_{est}$) difference. Thus, the algorithm also identifies drift when dPAP drops below zero and thus exceeds a drift threshold.

Returning to FIG. 8, if the drift threshold is not exceeded, then the one or more processors continue to obtain first and second patient characteristics of interest from the implantable pressure sensor. However, if the drift threshold is exceeded, then at 810, the one or more processors communicate an alert to a clinician. In one example the clinician is at a remote location such as a clinician office, hospital or the like and receives the alert via a wireless communication protocol. The alert may be a message that identifies the implantable pressure sensor and the patient and indicates that calibration is required. The message can be a code, color, sound, chart, or the like that alerts the clinician that patient with the implantable pressure sensor should visit the clinician (or the clinician should visit the patient) to determine if calibration is needed. In one example, an appointment is automatically scheduled at the clinician's office. The one or more processors may access the calendar of both the patient and the clinician to provide a time. Alternatively, based on the amount of drift detected, a recommendation may be provided for a timeline (e.g., within a week, within a month, within two months) for the patient to visit the clinician.

In one example, the difference (i.e., error) of $|mPAP-mPAP_{est}|$ can be displayed to the clinician, indicating the estimated magnitude of the drift. The drift detection "sensitivity" can be programmable (e.g., low, medium, high) by adjusting the drift threshold (e.g., 10, 15, 20 mmHg). This may be critical when this methodology is used in conjunction with another algorithm, and a high drift detection sensitivity is required (lower difference threshold) to refrain from providing medication recommendations for all sensors in which drift is suspected.

At 812, the implantable pressure sensor is tested by a clinician to determine whether calibration of the implantable pressure sensor is required. In one example, an RHC value is measured. By having the implantable pressure sensor system disclosed that provides an alert upon a detection that a drift threshold has been exceeded, instead of just measuring the RHC value at a next visit to the clinician, the RHC value is measured concurrently (e.g., within a few day or a few weeks) with the detection of the drift threshold being exceeded. This can result in the reduction of hundreds of days from detection of the implantable pressure sensor that requires calibration. As a result, false readings and medications are avoided.

At 814, if confirmation is provided that the implantable pressure sensor has experienced drift, then the one or more processors calibrate the implantable pressure sensor. By calibrating the implantable pressure sensor, accurate readings can again be obtained, reducing incorrect diagnosis and treatments.

With relation to the method of FIG. 8 the algorithm, including the configurable implantable pressure sensor parameters used, is described as follows:

1. The baseline ratio ($R_0$) is defined as the median of the ratio (R=[sPAP−dPAP]/mPAP) calculated from all readings collected from days 7-14 post-implant/calibration.
2. For each subsequent reading, $mPAP_{est}$ is calculated using the R0 and the reading's pulse pressure: $mPAP_{est}=(sPAP-dPAP)/R_0$
3. The absolute mPAP difference ($Diff_{med}$) is then calculated for each reading as the median difference of $|mPAP-mPAP_{est}|$ across all readings in the previous 21 days (i.e., 3-week moving median). Note that the median is only calculated for days with 4+ readings available in the previous 3-week window.
4. Likewise, the dPAP median ($dPAP_{med}$) is calculated for each reading as the median dPAP across all readings in the previous 21 days (i.e., 3-week moving median). Note that the median is only calculated for days with 4+ readings available in the previous 3-week window.
5. In one example drift is identified when either of the following drift thresholds are satisfied:

$$Diff_{med} \geq 15 \text{ mmHg} \quad \text{a.}$$

$$dPAP_{med} < 0 \text{ mmHg} \quad \text{b.}$$

6. If/when the sensor is recalibrated, the baseline ratio is recalculated (median ratio of all readings 7-14 days post-calibration).

When using the database of implantable pressure sensors described in relation to FIGS. 2-7 the methodology of FIG. 8 was utilized to determine if drift existed in implantable pressure sensors at an RHC follow up when the drift threshold was exceeded. Each sensor was then classified as follows:

TP (true positive): Drift was observed at the time of RHC follow-up, and drift was identified by the algorithm at any time from implant to RHC follow-up.

TN (true negative): Drift was not observed at the time of RHC follow-up, and drift was not identified by the algorithm at any time from implant to RHC follow-up.

FP (false positive): Drift was not observed at the time of RHC follow-up, but drift was identified by the algorithm at any time from implant to RHC follow-up.

FN (false negative): Drift was observed at the time of RHC follow-up, but drift was not identified by the algorithm at any time from implant to RHC follow-up.

Using these classifications, the following performance metrics were calculated:

Sensitivity=% of drifted sensors that were accurately detected=TP/(TP+FN)

Specificity=% of non-drifted sensors that were accurately detected=TN/(TN+FP)

Positive Predictive Value (PPV)=% of drift-detected sensors that truly drifted=TP/(TP+FP)

Negative Predictive Value (NPV)=% of non-drift detected sensors that truly did not drift=TN/(TN+FN)

Drift Detection Benefit=#days prior to RHC follow-up that the algorithm appropriately detected drift (for TP only)

For the 386 sensors evaluated as part of the US PER database, 74 TPs, 21 FPs, 211 TNs, and 78 FNs were identified. The resulting performance metrics are as follows:

Sensitivity=48.7%

Specificity=90.9%

PPV=77.9%

NPV=73.0%

Drift Detection Benefit=median 290.5 days (IQR: 116, 531 days)

Although the algorithm only identified 48.7% of sensors that ultimately exhibited drift at the time of RHC (sensitivity), 77.9% of all sensors identified as having drifted by the algorithm did truly drift (PPV). In those sensors, the drift was identified 290.5 days earlier than the RHC procedure, potentially avoiding inaccurate diagnoses or medication changes.

Figure 12:
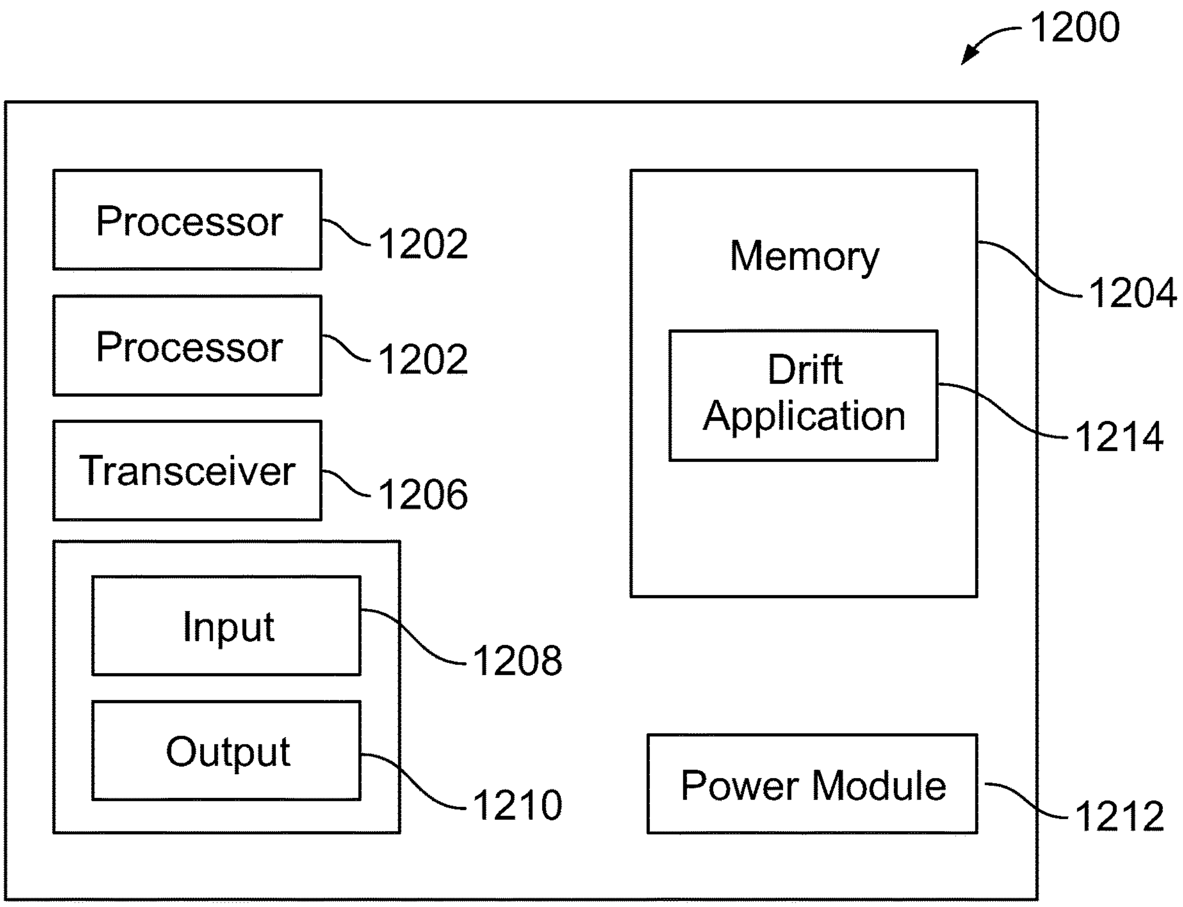
FIG. 12 illustrates a schematic block diagram of a control system for an implantable pressure sensor in accordance with the embodiments herein.

FIG. 12 illustrates a simplified block diagram of a controller 1200 that is configured to implement the methodologies of FIGS. 2 and 8 to alert a clinician that recalibration of an implantable pressure sensor is required. The controller may be part of an implantable pressure sensor, an implantable medical device (IMD) in communication with the implantable pressure sensor, within a control system (e.g., as in FIG. 13) that includes the implantable pressure system, an external device that communicates with the implantable pressure sensor, or the like.

The controller 1200 includes components such as one or more processors 1202 (e.g., a microprocessor, microcomputer, application-specific integrated circuit, etc.), one or more local storage medium (also referred to as a memory portion) 1204, one or more transceivers 1206, one or more input devices 1208 and one or more output devices 1210, a power module 1212 and drift application 1214. All of these components can be operatively coupled to one another, and can be in communication with one another, by way of one or more internal communication links, such as an internal bus.

The local storage medium 1204 can encompass one or more memory devices of any of a variety of forms (e.g., read only memory, random access memory, static random-access memory, dynamic random-access memory, etc.) and can be used by the processor 1202 to store and retrieve data. The data that is stored by the local storage medium 1204 can include, but not be limited to, CA signals, acceleration signals, impedance data, sets of data values, algorithms, applications, or the like. The local storage medium 1204 can also include executable code that controls basic functions of the external device 1200, such as interaction among the various components, communication with IMDs via the transceiver 1206 and storage and retrieval of applications and context data to and from the local storage medium 1204. The transceiver 1206 may provide wire communication, wireless communication, cellular communication, over the air communication, network communication, electronic communication, a combination thereof, or the like.

In one example embodiment, the local storage medium includes the drift application 1214. The drift application 1214 includes instructions for obtaining characteristics of interest of a patient and/or implantable pressure sensor and utilizing the characteristics of interest to determine an implantable pressure sensor parameter that can be used to determine whether a drift threshold has been exceeded. In making these determinations algorithms, artificial intelligence algorithms, numerical methods, functions, models, or the like can be utilized to determine the implantable pressure sensor parameter and/or whether the drift threshold has been exceeded. In one example, a numerical method such as the WD may be used. In other examples, Hoeffding's Bound (numerical) method is utilized, whereas alternatively an estimated pressure difference between systolic and diastolic pressures is determined. To this end, the drift application 1214 can include all the calculations, determinations, etc. presented related to the methods of FIGS. 2 and 8.

Figure 13:
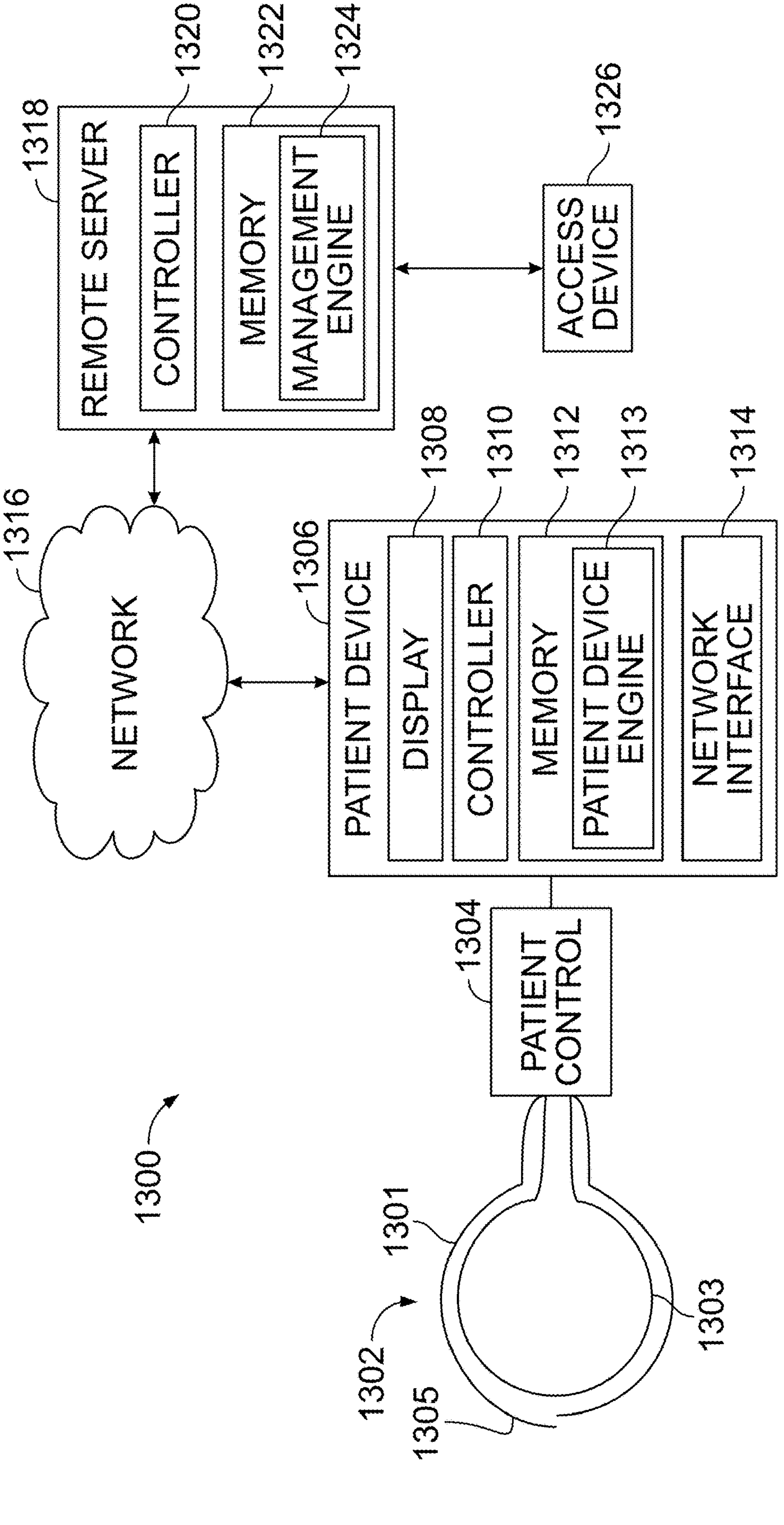
FIG. 13 illustrates embodiments for implementing the controller of FIG. 12 within a data acquisition and management system.

FIG. 13 illustrates embodiments for implementing the controller of FIG. 12 within a data acquisition and management system 1300 such as described in U.S. Pat. No. 8,111,150 (incorporated by reference above). The controller of FIG. 12 can be implemented in the system 1300 to determine an estimated drift for readings or measurements obtained by an implantable pressure sensor. The system 1300 includes an acquisition device such as an antenna 1302. The antenna 1302 includes a transmit loop 1301 and a receive loop 1303. The transmit loop 1301 may include a discontinuous area 1305 that can form a capacitor, as described below.

The antenna 1302 connects to a patient control device 1304 over wires, wirelessly or otherwise. The patient control device 1304 allows the patient to initiate interrogation of the implanted sensor (e.g., pressure sensor).

The antenna 1302 and/or patient control device 1304 may also be in communication with a patient device 1306. The patient device 1306 may monitor various activities of acquiring data from the implanted sensor, such as by monitoring the existence and strength of the energizing and implanted sensor signal and include a display 1308 to display instructions, status of data acquisition or other information to the patient. As illustrated in FIG. 13, the patient control device 1304 may be separate from the patient device 1306. In some embodiments, the patient device 1306 includes the patient control device 1304. In other embodiments, the antenna 1302 includes the patient control device 1304. The patient device 1306 also includes a controller 1310 (e.g., one or more processors) and a computer-readable memory, such as memory 1312. The controller 1310 is configured to implement all or portions of the methodologies of FIGS. 2 and 8 to alert a clinician that recalibration of an implantable pressure sensor is required.

Memory 1312 may include executable code (e.g., program instructions), such as a patient device engine 1313. The patient device engine 1313 may be adapted to receive data from the antenna 1302, display instructions or other information on the display 1308, convert data to digital data and/or format implanted sensor data into a data file to send over a network. The implanted sensor data and/or data file may be stored in memory 1312. The antenna 1302, patient control device 1304, and patient device 1306 may be located in and/or outside a hospital or other medical facility. For example, these devices may be located at the patient's home.

The patient device 1306 also includes a network interface 1314, such as an Ethernet port, modem port or other network port adapter. The network interface 1314 is adapted to connect to network 1316 and to send the data file to a remote server 1318 over the network 1316. The network 1316 may include one or a combination of any type of network such as LAN, WAN, WLAN, public switched telephone network, GSM, or otherwise. The remote server 1318 receives the data file and includes controller 1320 (e.g., one or more processors) and a computer-readable memory, such as memory 1322. The controller 1320 is configured to implement all or portions of the methodologies of FIGS. 2 and 8 to alert a clinician that recalibration of an implantable pressure sensor is required.

Memory 1322 can store the data file and includes computer-executable code, such as a management engine 1324. The management engine 1324 may periodically, such as once per minute, scan the data files stored in the memory 1322 to determine whether new or additional data is in the memory 1322. In some embodiments, the management engine 1324 can format the data file into various forms and notify pre-determined authorized persons on a user list stored in the memory 1322, such as by electronic mail, that a new data file is present and ready for review.

Physicians or authorized persons may use an access device 1326, such as a computer system, to access the data file and/or formatted data in the remote server memory 1322. For example, the access device 1326 may access a web interface that authenticates the access device users and allows the users to view and manage the patient data, view patient data histories, set automatic alert ranges to alert the authorized user when the patient data exceeds set levels, or any other function associated with viewing, managing, and analyzing the data file.

The system of FIG. 13 can be used to implement the methods of FIG. 2 and FIG. 8. For example, the controller 1320 and/or controller 1310 can continuously obtain first and second patient characteristics of interest (202) from the implantable pressure sensor. The controller 1320 and/or controller 1310 can quantify the distance mPAP between the sPAP and dPAP utilizing a first numerical method in real time (204). The controller 1320 and/or controller 1310 can determine whether a drift threshold has been exceeded based on the mPAP measurement (206). If the drift threshold is exceeded, the controller 1320 and/or controller 1310 can communicate an alert (208) such as by communicating an alert to an access device 126, text, email, phone, etc. If confirmation is provided that the implantable pressure sensor has experienced drift, then the controller 1320 and/or controller 1310 can calibrate the implantable pressure sensor (212). In some embodiments, the controller 1320 and/or controller 1310 can calibrate the implantable pressure sensor 212 based on input received.

In another embodiment, the controller 1320 and/or controller 1310 can calculate a ratio (R=[sPAP−dPAP]/mPAP) when an implantable pressure sensor is implanted into a patient and before any drift has occurred (802). The controller 1320 and/or controller 1310 can continuously obtain first and second patient characteristics of interest (804) from the implantable pressure sensor. The controller 1320 and/or controller 1310 can continuously determine an implantable pressure sensor parameter that is R=[sPAP−dPAP]/mPAP) in real time based on the obtained first and second patient characteristics (806) and determine whether a drift threshold has been exceeded based on the ratio (808). If the drift threshold is exceeded, the controller 1320 and/or controller 1310 communicates an alert (810) to a clinician. In one example the clinician is at a remote location such as a clinician office, hospital or the like and receives the alert via a wireless communication protocol. If confirmation is provided that the implantable pressure sensor has experienced drift, then the controller 1320 and/or controller 1310 calibrates the implantable pressure sensor (814).

In some embodiments, the controller 1320 and/or controller 1310 can receive, from an implantable pressure sensor, characteristics of interest related to a patient and determine an implantable pressure sensor parameter in real time based on the characteristics of interest related to a patient. The controller 1320 and/or controller 1310 can provide a drift threshold related to the implantable pressure sensor parameter, determine whether the drift threshold has been exceeded based on the implantable pressure sensor parameter, and communicate an alert in response to determining the drift threshold has been exceeded. In some cases, the alert can be communicated to the access device 126.

In some embodiments, the controller 1320 and/or controller 1310 can determine the implantable pressure sensor parameter by using a first numerical method in real time using the characteristics of interest received from the implantable pressure sensor. In some cases, the controller 1320 and/or controller 1310 can determine whether the drift threshold has been exceeded by utilizing a second numerical method using the parameter determined using the first numerical method. In other cases, the one or more processors 3120 of the remote server 1318 can dynamically update the drift threshold in real time based on the characteristics of interest received from the implantable pressure sensor. In still further embodiments, the drift threshold is manually input into the access device 1326 or the patient device 1306 or is a predefined drift threshold.

Closing

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network, and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving, and accessing structured or unstructured data. Database servers may include table-based servers, document-based servers, unstructured servers, relational servers, non-relational servers, or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer, or speaker). Such a system may also include one or more storage devices, such as disk drives, optical storage devices and solid-state storage devices such as random-access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being conducted in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112 (f), unless and until such claim limitations expressly use the phrase "means for" followed by a statement of function void of further structure.

What is claimed is:

1. A controller for calibrating an implantable pressure sensor, comprising:
- one or more processors; and
- a memory coupled to the one or more processors, wherein the memory stores program instructions, wherein the program instructions are executable by the one or more processors to:
- receive, from an implantable pressure sensor, first and second characteristics of interest (COI) related to a patient;
- calculate an implantable pressure sensor parameter in real time based on a difference between the first and second characteristics of interest related to a patient, wherein the implantable pressure sensor parameter represents a reference that remains accurate regardless of drift;
- provide a drift threshold related to the implantable pressure sensor parameter;
- determine whether the drift threshold has been exceeded based on the implantable pressure sensor parameter; and
- communicate an alert in response to determining the drift threshold has been exceeded.

2. The controller of claim 1, wherein the first and second characteristics of interest represent a systolic pulmonary artery pressure (sPAP) and a diastolic pulmonary artery pressure (dPAP), respectively.

3. The controller of claim 2, wherein the implantable pressure sensor parameter is a distance between a dPAP and a sPAP (mPAP).

4. The controller of claim 1, wherein the one or more processors are located remotely with respect to the implantable pressure sensor.

5. The controller of claim 1, wherein to determine whether the drift threshold has been exceeded comprises utilizing a numerical method using the parameter determined using the first numerical method.

6. The controller of claim 5, wherein the second numerical method includes utilizing a Hoeffding's Bound method.

7. The controller of claim 1, wherein the one or more processors are further configured to dynamically update the drift threshold in real time based on the first and second characteristics of interest received from the implantable pressure sensor.

8. The controller of claim 1, wherein the drift threshold is manually input to the controller.

9. The controller of claim 1, wherein the one or more processors are further configured to determine the implantable pressure sensor parameter, at least in part, by determining a pulse pressure as the difference, different, the pulse pressure representing the reference that remains accurate regardless of drift.

10. The controller of claim 9, wherein the one or more processors are further configured to determine the implantable pressure sensor parameter based on a relation between the pulse pressure and at least one of the first and second characteristics of interest.

11. The controller of claim 1, wherein the one or more processors calculate the implantable sensor pressure parameter and determine whether the drift threshold has been exceeded daily over a life of the implantable pressure sensor.

12. A method for calibrating an implantable pressure sensor comprising:
- obtaining, from the implantable pressure sensor, first and second characteristics of interest related to a patient;
- calculating, with a controller, an implantable pressure sensor parameter in real time based on a difference between the first and second characteristics of interest related to the patient, wherein the implantable pressure sensor parameter represents a reference that remains accurate regardless of drift;
- obtaining a drift threshold related to the implantable pressure sensor parameter;
- determining, with the controller, whether the drift threshold has been exceeded based on the implantable pressure sensor parameter; and
- recalibrating, with the controller, the implantable pressure sensor.

13. The method of claim 12, further comprising:
- communicating, with the controller, an alert in response to determining the drift threshold has been exceeded.

14. The method of claim 13, further comprising:
- conducting an invasive right heart catheterization (RHC) in response to receiving the alert to verify the drift threshold has been exceeded; and
- recalibrating the implantable pressure sensor in response to verifying the drift threshold has been exceeded by the RHC.

15. The method of claim 13, wherein determining whether the drift threshold has been exceeded comprises utilizing a second numerical method using the parameter determined using the first numerical method.

16. The method of claim 12, wherein obtaining the drift threshold comprises dynamically updating the drift threshold in real time based on the first and second characteristics of interest related to the patient.

17. The method of claim 12, further comprising determining the implantable pressure sensor parameter, at least in part, by determining a pulse pressure as the difference, the pulse pressure representing the reference that remains accurate regardless of drift.

18. The method of claim 17, further comprising determining the implantable pressure sensor parameter based on a relation between the pulse pressure and at least one of the first and second characteristics of interest.

19. The method of claim 12, further comprising calculating the implantable sensor pressure parameter and determining whether the drift threshold has been exceeded daily over a life of the implantable pressure sensor.

20. A computer program product comprising a non-transitory computer readable storage medium comprising computer executable code to:
- obtain first and second characteristics of interest related to a patient from an implantable pressure sensor;
- calculate an implantable pressure sensor parameter in real time based on a difference between the first and second characteristics of interest related to the patient, wherein the implantable pressure sensor parameter represents a reference that remains accurate regardless of drift;
- provide a drift threshold related to the implantable pressure sensor parameter;
- determine whether the drift threshold has been exceeded based on the implantable pressure sensor parameter;
- communicate an alert in response to determining the drift threshold has been exceeded; and
- calibrate the implantable pressure sensor based on the alert.

21. The computer program product of claim 20, wherein to determine whether the drift threshold has been exceeded comprises utilizing a second numerical method using the parameter determined using the first numerical method.

22. The computer program product of claim 20, wherein to provide the drift threshold, the drift threshold is dynamically calculated in real time.

23. The computer program product of claim 20, wherein to provide the drift threshold, the drift threshold is received from a manual input.

* * * * *